US008993242B2

(12) United States Patent
Han et al.

(10) Patent No.: US 8,993,242 B2
(45) Date of Patent: Mar. 31, 2015

(54) METHOD FOR FUNCTIONAL TESTING OF SITE-SPECIFIC DNA METHYLATION

(75) Inventors: Weiguo Han, Albany, NY (US); Simon D. Spivack, Sleepy Hollow, NY (US); Miao Kevin Shi, Flushing, NY (US)

(73) Assignee: Albert Einstein College of Medicine of Yeshiva University, Bronx, NY (US)

(*) Notice: Subject to any disclaimer, the term of this patent is extended or adjusted under 35 U.S.C. 154(b) by 700 days.

(21) Appl. No.: 13/349,745

(22) Filed: Jan. 13, 2012

(65) Prior Publication Data

US 2012/0183961 A1 Jul. 19, 2012

Related U.S. Application Data

(60) Provisional application No. 61/461,239, filed on Jan. 14, 2011.

(51) Int. Cl.
C12Q 1/68 (2006.01)
C12P 19/34 (2006.01)

(52) U.S. Cl.
CPC ................................ *C12Q 1/6869* (2013.01)
USPC ........................................ 435/6.12; 435/91.2

(58) Field of Classification Search
USPC ............................................... 435/6.12, 91.2
See application file for complete search history.

(56) References Cited

U.S. PATENT DOCUMENTS 5,858,671 A * 1/1999 Jones ............................ 435/6.18
6,017,701 A * 1/2000 Sorge et al. .................. 435/6.14

OTHER PUBLICATIONS

Graessmann et al., Molecular and Cellular Biology 14(3), 2004-2010 (1994).*
Castanotto et al., Mol. Ther.12;179-183, (2005).
Curradi et al. "Molecular Mechanisms of Gene Silencing Mediated by DNA Methylation," Mol. Cell Biol. 22, 3157-3173, (2002).
Kawasaki et al., Nature 431; 211, (2004).
Kawasaki et al., Nature 441; 1176, (2006).
Li et al., Nucleic Acids Res.35:100-112, (2007).
Meister et al., Nucleic Acids Res. 38:1749-59 (2010).
Morris et al., Science. 305:1289-92, (2004).
Suzuki et al., J. RNAi Gene Silencing 1; 66-78, (2005).
Smith et al., J. Biol. Chem. 283: 9878-9885, (2008).
Smith et al., Nucleic Acids Res. 35:740-754, (2007).

* cited by examiner

*Primary Examiner* — Kenneth Horlick
(74) *Attorney, Agent, or Firm* — Amster, Rothstein & Ebenstein LLP

(57) ABSTRACT

Methods and kits are provided for testing the functional effect of methylating different cytosine residues, for testing patterns of DNA methylation on gene expression, and for site-specific methylation, as well as methylated DNA constructs. Methods are provided that include steps of denaturing a circular double-stranded DNA construct; hybridizing primers to separate strands of the denatured circular DNA construct; contacting the hybridized primers with a DNA polymerase, deoxynucleoside triphosphates, and copies of the primers; contacting nicked copies with a DNA ligase so as to form a copy of the circular DNA construct; contacting the copy of the circular DNA construct with a methyltransferase enzyme; transfecting a cell with C-5 methylated circular DNA construct; and quantifying expression of a gene of interest, thereby determining the effect of C-5 methylating cytosine nucleotide residues of DNA on expression of the gene of interest.

20 Claims, 7 Drawing Sheets

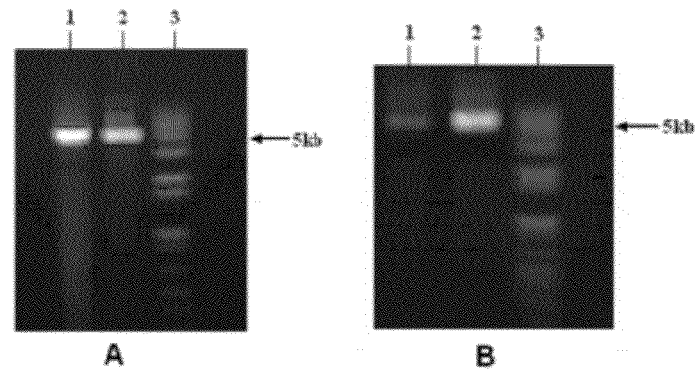
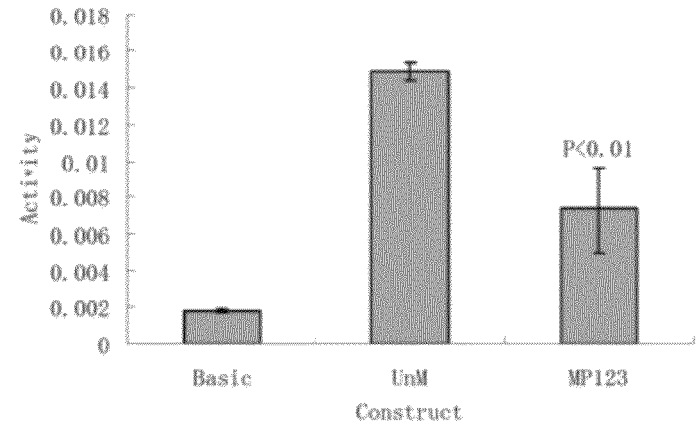
Figs. 4A-4C

METHOD FOR FUNCTIONAL TESTING OF SITE-SPECIFIC DNA METHYLATION

CROSS-REFERENCE TO RELATED APPLICATIONS

This application claims benefit of U.S. Provisional Application No. 61/461,239, filed Jan. 14, 2011, the contents of which are hereby incorporated by reference.

STATEMENT OF GOVERNMENT SUPPORT

This invention was made with government support under grant numbers CA 104812, CA 121068, and CA 145422 awarded by the National Institutes of Health. The government has certain rights in the invention.

BACKGROUND OF THE INVENTION

Throughout this application various publications are referred to by author and year of publication. Full citations for these references may be found at the end of the specification. The disclosures of these publications are hereby incorporated by reference in their entirety into the subject application to more fully describe the art to which the subject invention pertains.

The ability to methylate specific DNA residues would be very useful. One aspect of the impact of testing DNA methylation impact on gene expression lies in the ability to measure the effect on gene expression of the myriad and complex DNA methylation patterns that have been observed in cells and tissues derived from humans and other organisms. The ability to methylate specific nucleotide residues of a DNA sequence, and test their functional significance, would help investigators focus on the most salient features of the methylome (the pattern and occurrence of methylation in the genome), on a gene-specific basis, for studies on the underpinnings of inheritance, development, gene regulation, environmental effects on gene regulation, and disease pathogenesis. Means for permitting the functional testing of the effect of different patterns of DNA methylation would be additionally useful for investigators.

Residue-specific DNA methylation in vitro or in vivo has not yet been achieved. Native DNA methylation is not preserved in PCR reactions. There exists a description of a patch DNA methylation strategy for functional testing as described in Curradi et al. (2002). For methylating DNA targets in chromatin (native chromosomes), where functional impact can be measured by measuring native gene or mRNA transcript expression, siRNA directed DNA methylation has been reported in plant and yeast. Kawasaki et al. reported siRNA could also direct DNA methylation in human cells (Nature 431; 211, 2004) but this paper was subsequently retracted (Nature 441; 1176, 2006). There are several papers supporting siRNA directed DNA methylation in human cells, albeit with spread of methylation beyond the target site (Morris et al., (2004); Castanotto et al., (2005); Suzuki et al., (2005)). Zinc finger-DNA methyltransferase fusion also can be used for site-directed DNA methylation in chromatin, but the limitation is that the flanks of the target site must have the zinc finger protein recognition sequences (Meister et al., (2010); Smith et al., (2008); Smith et al., (2007); Li et al., (2007)). The limitations inherent to these technologies (imprecision in target sites methylated by siRNA, and target sequence limitations by Zn finger approaches) have not yet been solved, nor have they been coupled to precise functional in vitro testing of their impact on gene expression.

The present invention addresses this need by providing a technique for methylating specific cytosines of CG dinucleotides ("CpG") in a given DNA and also measuring the impact of that de novo methylation on gene expression.

SUMMARY OF THE INVENTION

A method for determining the effect of C-5 methylating one or more predetermined cytosine nucleotide residues of a deoxyribonucleic acid on expression of a gene of interest comprising the steps of:

a) denaturing a circular double-stranded deoxyribonucleic acid construct (circular DNA construct), wherein a cytosine residue of one of the strands of the circular DNA construct corresponds to the predetermined cytosine nucleotide residue and wherein the circular DNA construct comprises a nucleotide sequence identical to the gene of interest;

b) hybridizing each of a pair of primers to separate strands of the denatured circular DNA construct, wherein each primer comprises a 5' phosphate, and wherein at least one of the primers is C-5 methylated at a cytosine nucleotide residue thereof which is (i) immediately 5' to a guanine nucleotide residue of the primer, and (ii) complementary to a guanine nucleotide residue of the strand of the circular DNA construct immediately 3' to the cytosine nucleotide residue of the DNA construct which corresponds to the predetermined cytosine nucleotide residue;

c) contacting the hybridized primers resulting from step b) with a DNA polymerase, deoxynucleoside triphosphates, and a plurality of copies of the pair of primers under conditions permitting a polymerase chain reaction to occur, thereby producing a plurality of nicked copies of the circular DNA construct, wherein each strand of each nicked copy incorporates a primer comprising a 5' phosphate and wherein at least one strand of each nicked copy incorporates the C-5 methylated primer;

d) contacting at least one copy of the plurality of nicked copies with a DNA ligase so as to form a phosphodiester bond between the 5' phosphate of each incorporated primer of each strand and each respective 3' end of each strand of the at least one copy so as to thereby form a copy of the circular DNA construct;

e) contacting the copy of the circular DNA construct with a methyltransferase enzyme so as to thereby C-5 methylate the cytosine nucleotide residue immediately 5' to the guanine nucleotide residue which is hybridized to, or opposite, the C-5 methylated cytosine nucleotide residue of the C-5 methylated primer incorporated into the copy of the circular DNA construct;

f) transfecting a cell with the C-5 methylated circular DNA construct resulting from step e); and g) quantifying expression by the cell of the gene of interest, thereby determining the effect of C-5 methylating the one or more predetermined cytosine nucleotide residues of the deoxyribonucleic acid on expression of the gene of interest.

A method for making a deoxyribonucleic acid which is C-5 methylated at a predetermined cytosine nucleotide residue thereof comprising the steps of:

a) denaturing a circular double-stranded deoxyribonucleic acid construct (circular DNA construct), wherein a cytosine residue of one of the strands of the circular DNA construct corresponds to the predetermined cytosine nucleotide residue;

b) hybridizing each of a pair of primers to separate strands of the denatured circular DNA construct, wherein each primer comprises a 5' phosphate, and wherein at least one of the primers is C-5 methylated at a cytosine nucleotide residue thereof which is (i) immediately 5' to a guanine nucleotide residue of the primer, and (ii) complementary to a guanine nucleotide residue of the strand of the circular DNA construct immediately 3' to the cytosine nucleotide residue of the DNA construct which corresponds to the predetermined cytosine nucleotide residue;

c) contacting the hybridized primers resulting from step b) with a DNA polymerase, deoxynucleoside triphosphates, and a plurality of copies of the pair of primers under conditions permitting a polymerase chain reaction to occur, thereby producing a plurality of nicked copies of the circular DNA construct, wherein each strand of each nicked copy incorporates a primer comprising a 5' phosphate and wherein at least one strand of each nicked copy incorporates the C-5 methylated primer;

d) contacting at least one copy of the plurality of nicked copies with a DNA ligase so as to form a phosphodiester bond between the 5' phosphate of each incorporated primer of each strand and each respective 3' end of each strand of the at least one copy so as to thereby form a copy of the circular DNA construct; and e) contacting the copy of the circular DNA construct with a methyltransferase enzyme so as to thereby C-5 methylate the cytosine nucleotide residue immediately 5' to the guanine nucleotide residue which is hybridized to, or opposite, the C-5 methylated cytosine nucleotide residue of the C-5 methylated primer incorporated into the copy of the circular DNA construct, so as to thereby make the deoxyribonucleic acid which is C-5 methylated at the predetermined cytosine nucleotide residue.

A method for determining the effect of C-5 methylating one or more predetermined cytosine nucleotide residues of cytosine-guanine dinucleotides of a deoxyribonucleic acid on expression of the deoxyribonucleic acid comprising C-5 methylating the one or more predetermined cytosine nucleotide residues by any of instant methods, and then quantifying the expression of the deoxyribonucleic acid, so as to thereby determine the effect of C-5 methylating the one or more predetermined cytosine nucleotide residues of cytosine-guanine dinucleotides of the deoxyribonucleic acid on expression of the deoxyribonucleic acid.

A method for inhibiting transcription of a gene of interest in a cell comprising transiently or stably transfecting the cell with a nucleic acid comprising a promoter, or regulatory element, or both, and a gene of interest, wherein the promoter, or regulatory element, or both, has been C-5 methylated at one or more predetermined cytosine nucleotide residue(s) of cytosine-guanine dinucleotides thereof by any of instant methods, so as to thereby inhibit transcription of the gene of interest in the cell.

A deoxyribonucleic acid comprising at least one cytosine nucleotide residue C-5 methylated by any of the instant methods.

A kit comprising a) a forward primer and a reverse primer specific for a gene of interest, wherein the primers are each phosphorylated at their 5' end and wherein at least one of the primers either (i) corresponds to a portion of a promoter region of the gene of interest or (ii) corresponds to the whole of the promoter region of the gene of interest, and is C-5 methylated at one or more predetermined cytosine nucleotide residues thereof, and b) a package insert providing instructions for using the primers in a process for making a double-stranded deoxyribonucleic acid construct which is C-5 methylated at a predetermined cytosine nucleotide residue corresponding to a promoter of the gene of interest.

BRIEF DESCRIPTION OF THE DRAWINGS

FIGS. 4-4C: A&B—PCR-ligase coupled amplification of DAPK reporter constructs. Two large 60-mer primers containing four methylated CpGs were used for PCR-ligase coupled amplification of DAPK reporter constructs (5011 bp). A. pfuUltra™ II Fusion HS DNA polymerase (Stratagene) (lane 1) and Herculase® II Fusion DNA polymerase (lane 2) were used to amplify the constructs along with Taq DNA ligase. B. PCR-ligation products were digested with Dpn1 and T7 exonuclease, lane 1: pfuUltra II Fusion HS DNA polymerase product; lane 2: Herculase II Fusion DNA polymerase product; lane 3: 1 kb plus DNA ladder. C. Unmethylated DAPK reporter constructs (unM) and 60-mer primer PCR methylated DAPK reporter constructs, combining the methylated sites from MP1 (three methylated CpG sites), MP2 (four sites) and MP3 (five sites) into one larger methylated oligo $MP_{123}$ (12 total methylated CpG sites) were transfected into A549 cells. Here, the CpGs methylated together in the $MP_{123}$ patch covered the region −120 to −10, reference to TSS, and appear to halve the Luc reporter expression, which is very similar to the MP1 patch alone (see FIG. 4). P values represent t test comparisons with the unmethylated DAPK reporter constructs (unM) control. Basic is empty vector.

DETAILED DESCRIPTION OF THE INVENTION

Figure 1:
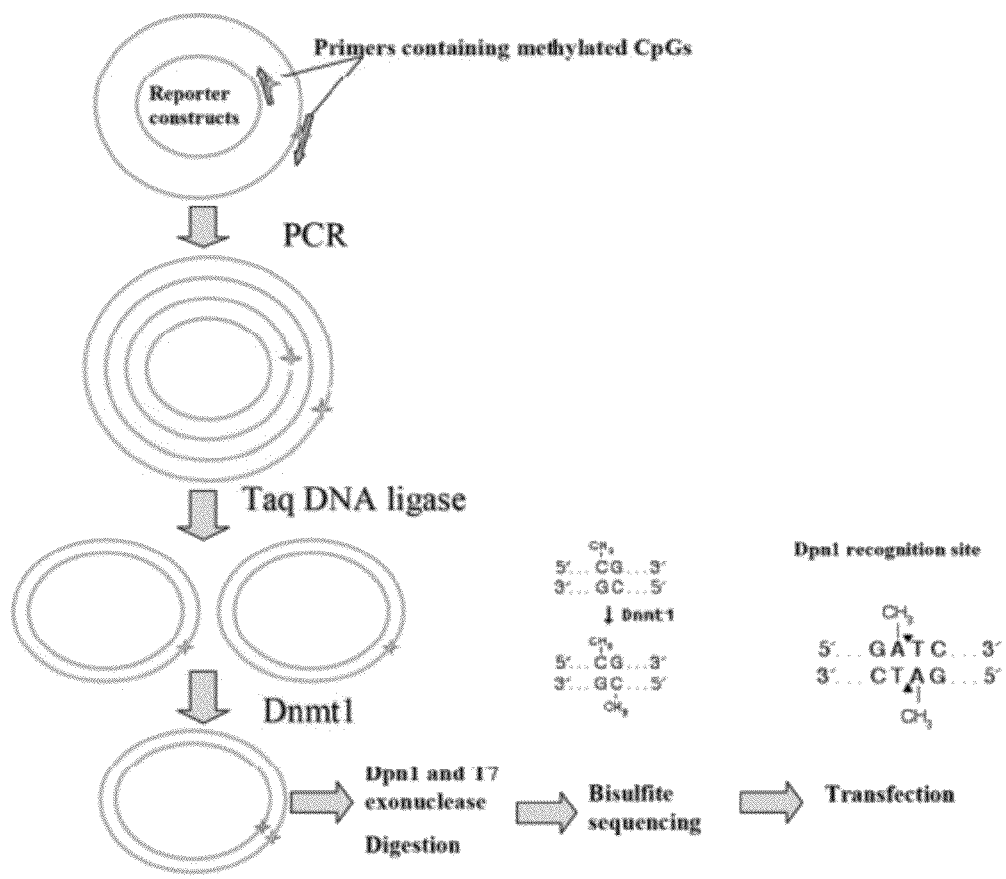
FIG. 1: Schema of strategy for site-specific DNA methylation. A pair of primers (arrows on top construct) containing methylated CpG (stars) are incorporated into the reporter construct with high-fidelity PCR and ligation. Dnmt1 is used to methylate the DNA strand complementary to the methylated primer. The parental DNA template is digested by Dpn1. The primers are phosphorylated at 5' end. Both primers are extended by high-fidelity DNA polymerase to generate new complementary strand DNA containing a nick. The new complementary strand DNA is ligated to form circular DNA by Taq DNA ligase. Dnmt1 is used to methylate the DNA strand complementary to the methylated primer. The parental DNA template is digested by Dpn1 which recognizes 5'-Gm6ATC-3' which are initially derived from *E. coli.* from the original template, and the linear DNA is digested by T7 exonuclease. The integrity of the intended methylated CpG sites is confirmed by bisulfite sequencing before transfection. The reporter constructs are transfected in eukaryotic cells for reporter readout.

A method is provided for determining the effect of C-5 methylating one or more predetermined cytosine nucleotide residues of a deoxyribonucleic acid on expression of a gene of interest comprising the steps of:
  a) denaturing a circular double-stranded deoxyribonucleic acid construct (circular DNA construct), wherein a cytosine residue of one of the strands of the circular DNA construct corresponds to the predetermined cytosine nucleotide residue and wherein the circular DNA construct comprises a nucleotide sequence identical to the gene of interest;
  b) hybridizing each of a pair of primers to separate strands of the denatured circular DNA construct, wherein each primer comprises a 5′ phosphate, and wherein at least one of the primers is C-5 methylated at a cytosine nucleotide residue thereof which is (i) immediately 5′ to a guanine nucleotide residue of the primer, and (ii) complementary to a guanine nucleotide residue of the strand of the circular DNA construct immediately 3′ to the cytosine nucleotide residue of the DNA construct which corresponds to the predetermined cytosine nucleotide residue;
  c) contacting the hybridized primers resulting from step b) with a DNA polymerase, deoxynucleoside triphosphates, and a plurality of copies of the pair of primers under conditions permitting a polymerase chain reaction to occur, thereby producing a plurality of nicked copies of the circular DNA construct, wherein each strand of each nicked copy incorporates a primer comprising a 5′ phosphate and wherein at least one strand of each nicked copy incorporates the C-5 methylated primer;
  d) contacting at least one copy of the plurality of nicked copies with a DNA ligase so as to form a phosphodiester bond between the 5′ phosphate of each incorporated primer of each strand and each respective 3′ end of each strand of the at least one copy so as to thereby form a copy of the circular DNA construct;
  e) contacting the copy of the circular DNA construct with a methyltransferase enzyme so as to thereby C-5 methylate the cytosine nucleotide residue immediately 5′ to the guanine nucleotide residue which is hybridized to the C-5 methylated cytosine nucleotide residue of the C-5 methylated primer incorporated into the copy of the circular DNA construct;
  f) transfecting a cell with the C-5 methylated circular DNA construct resulting from step e); and
  g) quantifying expression by the cell of the gene of interest, thereby determining the effect of C-5 methylating the one or more predetermined cytosine nucleotide residues of the deoxyribonucleic acid on expression of the gene of interest.

The method may be applied, mutatis mutandis, to a linear DNA also.

Step e) results in completing the hemi-methylation (e.g. initial strand) by methylating the C-5 of the complementary DNA strand, yielding two complementary strands methylated at the desired locus. Optionally, step e) can be omitted so as to achieve a hemi-methylated construct, in which case in step f) the circular DNA construct resulting from step d) is transfected into the cell. In an embodiment the nucleotide sequence identical to the gene of interest of the DNA construct comprises the cytosine residue corresponding to the predetermined cytosine nucleotide residue.

In an embodiment, the quantified expression of the gene of interest in step g) is compared to a quantified expression of the gene of interest of a non-C-5 methylated control.

A method is provided for making a deoxyribonucleic acid which is C-5 methylated at a predetermined cytosine nucleotide residue thereof comprising the steps of:
  a) denaturing a circular double-stranded deoxyribonucleic acid construct (circular DNA construct), wherein a cytosine residue of one of the strands of the circular DNA construct corresponds to the predetermined cytosine nucleotide residue;
  b) hybridizing each of a pair of primers to separate strands of the denatured circular DNA construct, wherein each primer comprises a 5' phosphate, and wherein at least one of the primers is C-5 methylated at a cytosine nucleotide residue thereof which is (i) immediately 5' to a guanine nucleotide residue of the primer, and (ii) complementary to a guanine nucleotide residue of the strand of the circular DNA construct immediately 3' to the cytosine nucleotide residue of the DNA construct which corresponds to the predetermined cytosine nucleotide residue;
  c) contacting the hybridized primers resulting from step b) with a DNA polymerase, deoxynucleoside triphosphates, and a plurality of copies of the pair of primers under conditions permitting a polymerase chain reaction to occur, thereby producing a plurality of nicked copies of the circular DNA construct, wherein each strand of each nicked copy incorporates a primer comprising a 5' phosphate and wherein at least one strand of each nicked copy incorporates the C-5 methylated primer;
  d) contacting at least one copy of the plurality of nicked copies with a DNA ligase so as to form a phosphodiester bond between the 5' phosphate of each incorporated primer of each strand and each respective 3' end of each strand of the at least one copy so as to thereby form a copy of the circular DNA construct; and
  e) contacting the copy of the circular DNA construct with a methyltransferase enzyme so as to thereby C-5 methylate the cytosine nucleotide residue immediately 5' to the guanine nucleotide residue which is hybridized to the C-5 methylated cytosine nucleotide residue of the C-5 methylated primer incorporated into the copy of the circular DNA construct,
  so as to thereby make the deoxyribonucleic acid which is C-5 methylated at the predetermined cytosine nucleotide residue.

The method may be applied, mutatis mutandis, to a linear DNA also.

Step e) results in completing the hemi-methylation (e.g. initial strand) by methylating the C-5 of the complementary DNA strand, yielding two complementary strands methylated at the desired locus. Optionally, step e) can be omitted so as to achieve a hemi-methylated construct.

In an embodiment, the instant methods further comprise subsequent to step e), digesting deoxyribonucleic acids in a reaction mixture resulting from steps a) through d) or steps a) through e) which deoxyribonucleic acids comprise a 5'-Gme6ATC-3' sequence by contacting the deoxyribonucleic acids which comprise a 5'-Gme6ATC-3' sequence with a Dpn1 enzyme under conditions permitting digestion of deoxyribonucleic acids.

In an embodiment of the instant methods, the DNA ligase is Taq DNA ligase. In an embodiment of the instant methods, the deoxynucleoside triphosphates are selected from dATP, dCTP, dGTP and dTTP.

In an embodiment, the instant methods further comprise (i) before step e) digesting linear deoxyribonucleic acids in a reaction mixture resulting from steps a) through d), or (ii) after step e) digesting linear deoxyribonucleic acids in a reaction mixture resulting from steps a) through e), by contacting the linear deoxyribonucleic acids in the reaction mixture with an exonuclease.

In an embodiment of the instant methods, the exonuclease is T7 exonuclease. In an embodiment of the instant methods, the methyltransferase enzyme is specific for hemi-methylated double-stranded DNA. In an embodiment of the instant methods, the methyltransferase enzyme is human DNA (cytosine-5) methyltransferase (Dnmt1). In an embodiment of the instant methods, the circular DNA construct comprises a promoter sequence. In an embodiment of the instant methods, the deoxyribonucleic acid which is C-5 methylated at the predetermined cytosine nucleotide residue is, or comprises, a promoter sequence. In an embodiment of the instant methods, a portion of the DNA construct comprises a nucleic acid sequence derived from *Escherichia coli*.

In an embodiment of the instant methods, at least one of the primers is from 18 to 30 nucleotide residues in length. In an embodiment of the instant methods, at least one of the primers is from 31 to 65 nucleotide residues in length.

In an embodiment of the instant methods, the DNA construct comprises a nucleic acid sequence encoding a reporter protein. In an embodiment of the instant methods, the reporter protein is a luciferase, a chloramphenicol transferase, a green fluorescent protein, a beta-galactosidase, or a recombinant human growth hormone, or other reporter/detectable gene. In an embodiment of the instant methods, at least one primer is C-5 methylated at the cytosine nucleotide residue of every cytosine-guanine dinucleotide thereof.

In an embodiment, the instant methods further comprise comprising bisulfite sequencing the deoxyribonucleic acid which is C-5 methylated at the predetermined cytosine nucleotide residue so as to confirm the C-5 methylation.

A method is provided for determining the effect of C-5 methylating one or more predetermined cytosine nucleotide residues of cytosine-guanine dinucleotides of a deoxyribonucleic acid on expression of the deoxyribonucleic acid comprising C-5 methylating the one or more predetermined cytosine nucleotide residues by any of instant methods, and then quantifying the expression of the deoxyribonucleic acid, so as to thereby determine the effect of C-5 methylating the one or more predetermined cytosine nucleotide residues of cytosine-guanine dinucleotides of the deoxyribonucleic acid on expression of the deoxyribonucleic acid.

A method is provided for determining the effect of C-5 methylating one or more predetermined cytosine nucleotide residues of cytosine-guanine dinucleotides of a deoxyribonucleic acid on expression of the deoxyribonucleic acid comprising. C-5 methylating the one or more predetermined cytosine nucleotide residues by any of instant methods, and then quantifying the expression of the deoxyribonucleic acid, so as to thereby determine the effect of C-5 methylating the one or more predetermined cytosine nucleotide residues of cytosine-guanine dinucleotides of the deoxyribonucleic acid on expression of the deoxyribonucleic acid.

A method is provided for inhibiting transcription of a gene of interest in a cell comprising transiently or stably transfecting the cell with a nucleic acid comprising a promoter, or regulatory element, or both, and a gene of interest, wherein the promoter, or regulatory element, or both, has been C-5 methylated at one or more predetermined cytosine nucleotide residue(s) of cytosine-guanine dinucleotides thereof by any of instant methods, so as to thereby inhibit transcription of the gene of interest in the cell.

In an embodiment of the instant methods, the cell is a mammalian cell. In an embodiment of the instant methods, the promoter has been C-5 methylated.

In an embodiment of the instant methods, the cell is stably transfected with the nucleic acid. In an embodiment of the instant methods, the cell is transiently transfected with the nucleic acid.

A deoxyribonucleic acid is provided comprising at least one cytosine nucleotide residue C-5 methylated by any of the instant methods.

A kit is provided comprising a) a forward primer and a reverse primer specific for a gene of interest, wherein the primers are each phosphorylated at their 5' end and wherein at least one of the primers either (i) corresponds to a portion of a promoter region of the gene of interest or (ii) corresponds to the whole of the promoter region of the gene of interest, and is C-5 methylated at one or more predetermined cytosine nucleotide residues thereof, and b) a package insert providing instructions for using the primers in a process for making a double-stranded deoxyribonucleic acid construct which is C-5 methylated at a predetermined cytosine nucleotide residue corresponding to a promoter of the gene of interest.

As used herein, a "predetermined" cytosine nucleotide residue is a cytosine nucleotide residue in a known nucleic acid sequence which is adjacent to a guanine nucleotide residue as a CG dinucleotide (commonly referred to as a CpG) and which is chosen to be methylated at its C-5 position. In the structure of the cytosine residue hereinbelow, the C-5 position of the cytosine is marked by an arrow.

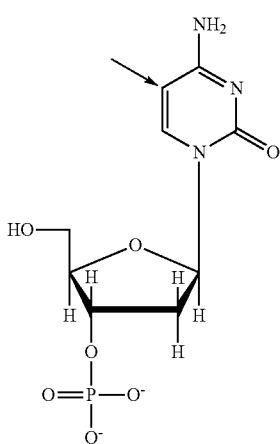

As used herein, dATP, dCTP, dGTP, and dTTP are deoxyadenosine triphosphate, deoxycytidine triphosphate, deoxyguanosine triphosphate, and thymidine triphosphate, respectively.

As used herein, a deoxyribonucleic acid construct is an artificially, constructed nucleic acid comprising at least a nucleic acid insert and a promoter within a vector. The construct may be used for transfecting the nucleic acid insert into a cell, so as, for example, to determine the effect of methylating specific CpG(s) in the promoter sequence on expression of the insert. As used herein, a circular DNA is a continuous nucleic acid having no 5' or 3' free end, being in the form of a circle. Constructs as disclosed herein are double-stranded.

As used herein, hybridizing a primer to each strand of a denatured DNA construct is a standard technique well known to one of ordinary skill in the art (for example, see PCR Primer: A Laboratory Manual, Second Edition, edited by Carl W. Dieffenbach and Gabriela S. Dveksler, Cold Spring Harbor Laboratory Press, 2003, ISBN 978-087969654-2, which is hereby incorporated by reference). Hybridizing a primer describes the binding of a primer of a given sequence to a portion of a nucleic acid, which portion has the complementary sequence to the given sequence, so as to permit primer extension to occur under DNA polymerization conditions.

As used herein, "denaturing" a double-stranded DNA means treating the DNA so as to separate it into individual strands, for example by application of heat as used in the polymerase chain reaction.

As used herein, "PCR" means polymerase chain reaction. The polymerase chain reaction is well-known in the art to amplify a single or a few copies of a piece of DNA across several orders of magnitude by use of thermal cycling, consisting of cycles of repeated heating and cooling of the reaction for DNA melting and enzymatic replication of the DNA and primers containing sequences complementary to the target region along with a DNA polymerase.

As used herein a "promoter" is a regulatory region of DNA, originally located upstream of a gene, providing a control point for regulated gene transcription. In an embodiment, the promoter is eukaryotic. In an embodiment, the promoter is prokaryotic. As used herein a regulatory element is a segment of DNA where regulatory proteins, such as transcription factors, bind preferentially.

As used herein, a "nicked copy" of a circular DNA construct means a nucleic acid having a sequence identical to the sequence of a strand of the circular DNA construct of which it is a copy except for the absence of a phosphodiester bond between the 3' terminal nucleotide residue of the nicked copy and the 5' terminal nucleotide residue of the nicked copy. The formation of a phosphodiester bond between the 3' terminal nucleotide residue and 5' terminal nucleotide residue, for example as effected by contacting the termini of the nicked copy with an appropriate DNA ligase when the 5' terminal nucleotide residue has been phosphorylated, permits formation of a circular DNA thereby removing the nick. Thus, a "copy of a circular DNA construct", i.e. with no "nicked" modifier, is a copy which is identical in sequence and pattern of bonds—i.e. it is not nicked.

As used herein "bisulfite sequencing" means any DNA sequencing technique involving a step of exposing the DNA to be sequenced to bisulfite, a deaminating agent, so as to convert the cytosine residues thereof, but not the 5-methylcytosine residues thereof, to uracil residues.

As used herein, a "gene of interest" means any genetic sequence which is coding DNA or which is coding and non-coding DNA, for example a gene. The genetic sequence can be obtained from one or more natural source(s) or be artificially synthesized or be a combination of both. The genetic sequence is "of interest" in that it is of interest to determine what, if any, the influence of C-5 methylation of one or more cytosine residues upstream of, or within, the genetic sequence is, especially on the expression thereof.

As used herein, to "transfect" a cell means to introduce genetic material into the cell so that it is transiently or stably transfected and permits expression of the genetic material by the cell. Transfection can be effected by means known in the art.

As used herein, cells (which are transfected by the methods described herein) include cells commonly used in the art for transfection. Accordingly, both eukaryotic and prokaryotic cells can be employed. In an embodiment, the cells are mammalian cells. In an embodiment the cells are a cell line such as, or derived from, in non-limiting examples, A549, HEK 293, 3T3, CHO, COS, HeLa, or Jurkat cells. In an embodiment the cells are, or are derived from, in non-limiting examples, keratinocytes, neural cells or prostate cells. In an embodiment the cells are *Xenopus* oocytes.

The term "immediately 5'" as used herein to describe the position of a first nucleotide residue relative to a second nucleotide residue means that the first nucleotide residue is bonded via a phosphodiester bond through the 3' carbon of its deoxyribose to the 5' carbon of the deoxyribose of the second nucleotide residue.

The term "immediately 3'" as used herein to describe the position of a first nucleotide residue relative to a second nucleotide residue means that the first nucleotide residue is bonded via a phosphodiester bond through the 5' carbon of its deoxyribose to the 3' carbon of the deoxyribose of the second nucleotide residue.

As used herein a "non-C-5 methylated control" is a control nucleic acid which is identical in sequence to the sequence to which it is being compared except that it has not been C-5 methylated at the one or more predetermined cytosine residues. Thus, the control may be transfected into cells etc. under identical conditions and the expression thereof quantified.

As used herein a nucleotide residue in a first nucleic acid which "corresponds to" a another nucleotide residue (in a second nucleic acid of the same sequence), for example as used in the phrase "wherein a cytosine residue of one of the strands of the circular DNA construct corresponds to the predetermined cytosine nucleotide residue", means that the nucleotide residue in the first nucleic acid is (i) of the same type (e.g. a cytosine) as the nucleotide residue to which it corresponds, and (ii) is in the same position in the sequence of the first nucleic acid as the position in the sequence in the second nucleic acid occupied by the nucleotide to which it corresponds. For example, in a parental DNA construct of sequence 5' ATTCG 3' the C residue "corresponds to" the C residue of a copy of the parental DNA construct having the sequence 5' ATTCG 3'.

As used herein, a primer is a short, chemically synthesized oligonucleotide which is designed to be hybridized to a target DNA and to permit initiation of DNA polymerization by a DNA polymerase. The primer can be of any suitable length that permits this function. The length of the primer will depend in part on the particular CpG(s) of the targeted nucleic acid to be methylated. In an embodiment the primer is from 18 to 70 nucleotides in length. In an embodiment the primer is from 18 to 25 nucleotides in length. In an embodiment the primer is from 26 to 40 nucleotides in length. In an embodiment the primer is from 41 to 55 nucleotides in length. In an embodiment the primer is from 56 to 70 nucleotides in length. In an embodiment one or both of the primers of a pair are 60 nucleotides in length.

Pairs of primers preferably have similar melting temperatures since annealing in a PCR will then occur for both simultaneously. Primer sequences are preferably chosen to uniquely select for a region of DNA to avoid mishybridization to a similar sequence. For example, a BLAST search may be used, e.g. see www.ncbi.nlm.nih.gov/tools/primer-blast/. In an embodiment, mononucleotide repeats are not preferred. Primers are preferably selected such that the primers used should not easily anneal with other primers in the mixture.

Where a numerical range is provided herein, it is understood that all numerical subsets of that range, and all the individual integers contained therein, are provided as part of the invention. Thus, a primer which is from 18 to 25 nucleotides in length includes the subset of primers which are 18 to 22 nucleotides in length, the subset of primers which are 20 to 25 nucleotides in length etc. as well as a primer which is 18 nucleotides in length, a primer which is 19 nucleotides in length, a primer which is 20 nucleotides in length, etc. up to and including a primer which is 25 nucleotides in length.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

Residue-specific DNA methylation in vitro or in vivo has not yet been achieved, whereby consequent functional impact on gene expression could be measured. A patch DNA methylation strategy exists as described in Curradi et al., 2002. There has been no further publication of that technique. The present inventors attempted to use the Curradi et al. technique as published to analyze promoter methylation, but were not successful with the outlined method. One major difficulty disclosed herein of the Curradi et al. technique is that the recombinant M13 construct is apparently too large (10 Kb) for T4 DNA polymerase to efficiently complete the synthesis of complementary strand DNA. Another is that working with single stranded constructs is very challenging in this context.

Herein a PCR-ligation-based protocol is disclosed. In an embodiment, unique to the disclosed protocol method, the PCR-ligation-based protocol does not need a single-stranded DNA template. This overcomes limitations of the Curradi et al. technique—the M13 phage components are not needed for reporter constructs. In addition, the constructs can be smaller, for example ~5 kb. Optimized PCR-ligation conditions are also disclosed herein. Demonstration that the promoter in the reporter constructs can be methylated in a site-specific manner with methylated PCR primers is disclosed herein, as is functional impact data (repression of the reporter).

RESULTS

Example 1

To methylate a specific CpG site in the promoter of reporter constructs, a site-specific DNA methylation technique is disclosed herein where a pair of primers, one or both of which contain synthetically methylated CpGs, is used to amplify the recombinant reporter construct with high-fidelity PCR (see FIG. 1).

The two primers can be 5'-end adjacent. The 5'-end of each primer is phosphorylated for ligation. The primers are extended during temperature cycling by high-fidelity DNA polymerase without strand-displacement activity, and each generates a new complementary strand of DNA containing a nick. The nick can be ligated by an appropriate ligase such as Taq DNA ligase. Following temperature cycling, the product is treated with an appropriate DNA methyltransferase, such as human DNA Methyltransferase (Dnmt1). Dnmt1 is specific for hemi-methylated DNA (FIG. 1) and is used to methylate the DNA strand complementary to the methylated primer. The parental DNA template is digested by an appropriate enzyme, such as Dpn1 which recognizes methylated 5'-G$^{me6}$ATC-3' sequences in the parental constructs derived from E. coli. The linear DNA is digested by an appropriate enzyme, such as a T7 exonuclease. The methylated CpG site can be verified by bisulfite genomic DNA sequencing.

Example 2

Figures 2A, 2B, 2C:
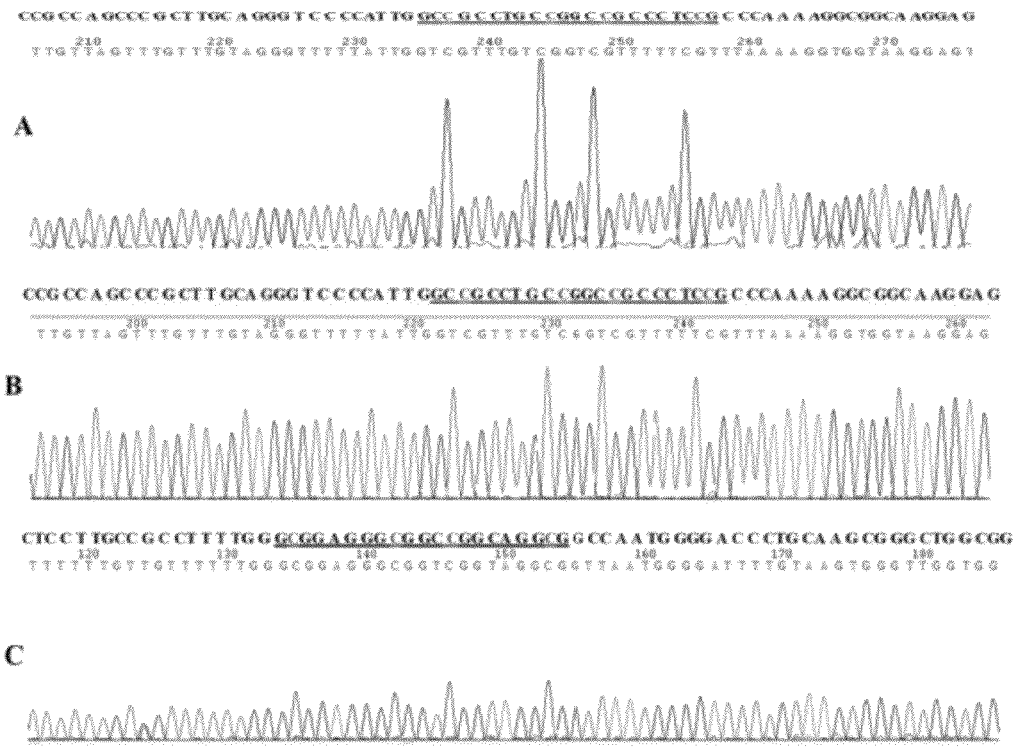
FIG. 2A-2C: Bisulfite sequencing of DAPK promoter in site-specific methylated reporter constructs. 100 ng of the site-specific methylated constructs was treated with bisulfite containing buffer. The promoter region was amplified with vector specific primers flanking the promoter. PCR product was subject to direct dideoxy-sequencing. The upper sequence (SEQ ID NO:1) of A is genome sequence in which the underlined target sequence contains four experimentally methylated cytosines (lower sequence is SEQ ID NO:2). In the bisulfite sequencing, all unmethylated cytosines are converted to thymine. Only the four target cytosines are methylated (see four highest peaks) in the bisulfite sequencing result. (A) The sequencing result before transfection into A549 cells. (B) The sequencing result after transfection into A549 cells for 36 hours (upper sequence is SEQ ID NO:3, lower sequence is SEQ ID NO:4). (C) The anti-sense strand sequencing result after transfection into A549 cells for 36 hours (upper sequence is SEQ ID NO:5, lower sequence is SEQ ID NO:6).

Demonstration of site-specific DNA methylation for DAPK promoter reporter construct: A 268 bp (−242~+25 nt) fragment of the DAPK promoter was inserted into PGL3-reporter constructs. The promoter could drive the reporter firefly luciferase gene expression in A549 cells. Two primers were designed for site-specific DNA methylation of the DAPK promoter in reporter constructs. The forward primer was 5'-gccgcctgccggccgccctccg-3' (SEQ ID NO:7) in which the four underlined cytosines are methylated. The reverse primer was 5'-caatggggaccctgcaagcgg-3' (SEQ ID NO:8) in which there are no methylated cytosines. The two primers were 5' end adjacent for complete amplification of the constructs and 5' end of each primer was phosphorylated for DNA ligation (see FIG. 1). The PCR-ligation reaction was optimized in 50 μl. 1× Herculase® II reaction buffer (Stratagene (now Agilent), Santa Clara, Calif.), 1 mM NAD+ (NEB, Ipswich, Mass.), 0.5 μl Herculase® II fusion DNA polymerase, 160 U Taq DNA ligase and 200 μM each dNTP, using 10 ng reporter constructs as template. Reaction conditions: denature at 98° C. for 2 min., then 98° C.×20 s, 60° C.×30 s, 72° C.×3 min., and 65° C.×5 min. for 26 cycles. The PCR-ligation product was purified with QIAquick® PCR purification kit (Qiagen, Valencia, Calif.) and subject to digestion with Dpn1 and T7 exonuclease overnight for removing the parental DNA and non-circular DNA. The circular DNA constructs containing the methylated primer were treated with Dnmt1 to methylate the complementary strand of the methylated primer. The site-specific methylated constructs were subject to bisulfite treatment and the promoter region was amplified for DNA sequencing. Results showed that the four target CpG sites were specifically methylated (FIG. 2).

Example 3

Figure 3:
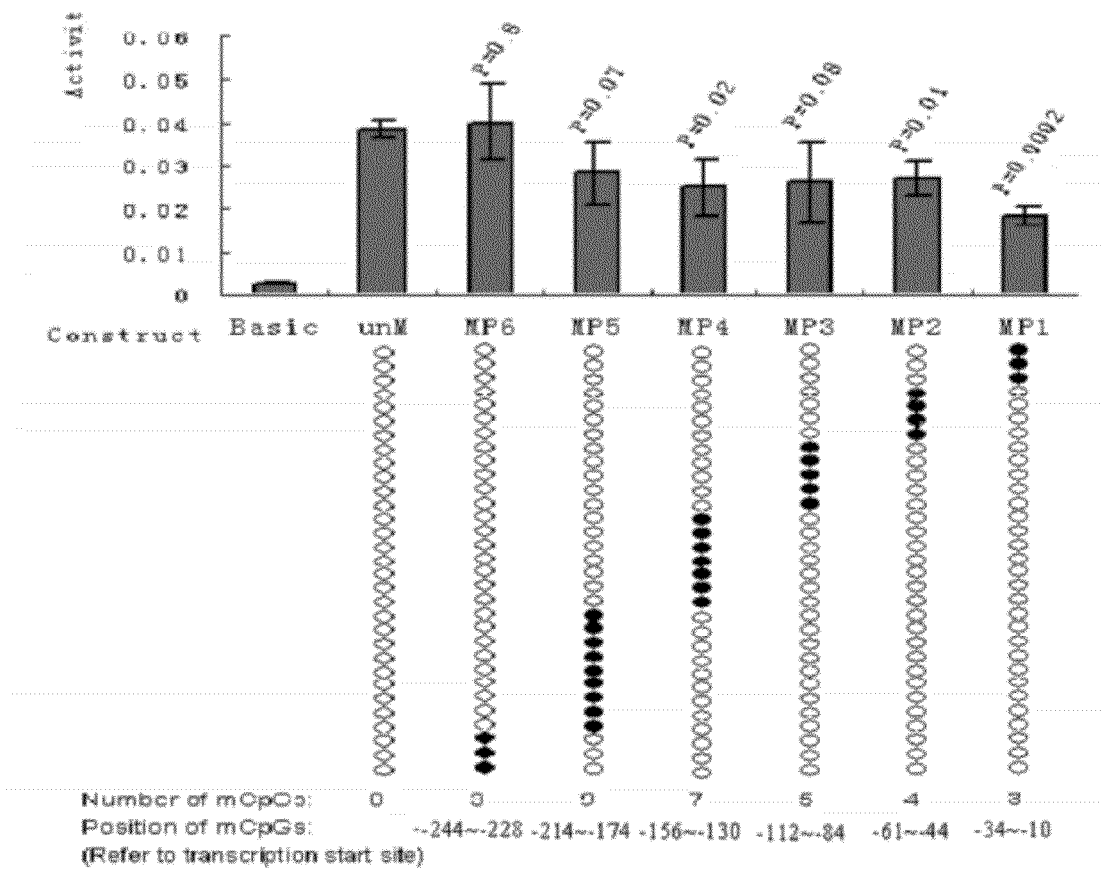
FIG. 3: Analysis of the effect of CpG methylation on DAPK promoter activity. Regions ~60 bp in length (30 bp forward and 30 bp reverse primers fit end-to-end) were tested. The numbers of methylated CpG sites were determined by the endogenous sequence in that 60 bp region (e.g. four CpGs at −10, −23 and −34 for MP1, three CpGs for MP2, five CpGs for MP3, seven CpGs for MP4, nine CpGs for MP5 and three CpGs for MP6). Unmethylated DAPK reporter constructs (unM) and six site-specific methylated DAPK reporter constructs (MP1 to MP6) were transfected into A549 cells, PRL-TK which expresses *Renilla* luciferase was co-transfected as an internal control for transfection efficiency. The empty vector (Basic) was also transfected as negative control. All constructs were transfected in triplicates. After 36 hours, luciferase activities were determined by a dual luciferase assay. Firefly luciferase activity is normalized to *Renilla* luciferase activity (internal control). Here, the most 3' cluster (the three CpGs methylated together by the MP1 patch, which covers the region −34 to −10, in reference to TIS) appear to halve the promoter activity. P values represent t-test comparisons with the unmethylated DAPK insert (unM) control. A separate set of replicate experiments on this same sequence revealed identical results (not shown). Basic: the reporter construct without promoter. unM: The reporter construct with unmethylated DAPK promoter. MP1 to MP6: reporter constructs with DAPK promoter methylated at different CpG sites. mCpG: Methylated CpG.

Functional analysis of DAPK promoter methylation: The functional impact of TIS-proximate promoter methylation of DAPK was analyzed by progressively methylating the promoter in synthesized reporter constructs. Six site-specific methylated DAPK promoter reporter constructs were created using six methylated PCR primers containing 3 to 9 methylated CpGs each (see Table 1). As controls, unmethylated PCR primers were used for creating unmethylated DAPK promoter reporter constructs by the same protocol. Site-specific methylated and unmethylated DAPK promoter reporter constructs were transfected into A549 cells. After 36 hours incubation, promoter activity was determined by a dual luciferase assay. Results showed that the methylation of the 3 CpGs (out of 31 CpGs in the promoter) closest to the transcription start site (TIS) produce a 54% decrease in promoter activity ($p<0.01$) as compared to the unmethylated DAPK promoter (FIG. 3). The methylation of the 12 CpG sites most upstream from the TIS had no significant effect on promoter activity.

TABLE 1

Primers for site-specific methylation of DAPK promoter reporter construct (SEQ ID NOS. 9-28 top to bottom, respectively):

| PCR primer | Sequence | Position |
| --- | --- | --- |
| DAPK-P1R | CACTCCGAAGCAGCCTCTCGGCTCCTTGCCGC | −5~−36 |
| DAPK-P1F | TGAGGAGGACAGCCGGACCGAGC | −4~+20 |
| DAPK-P2R | TGGGCGGAGGGCGGCCGGCAGGCGG | −40~−63 |
| DAPK-P2F | AAAGGCGGCAAGGAGCCGAGAGGC | −39~−16 |
| DAPK-P3R | GCAAGCGGGCTGGCGGCGCGGCCCACCCACCTCCGA | −79~−114 |
| DAPK-P3F | AGGGTCCCCATTGGCCGCCTGCCG | −78~−56 |
| DAPK-P4R | CAGGCCGGCGCTGCGGGTTCTGCGCGGCGCTCGC | −125~−158 |
| DAPK-P4F | GCAGGGCAGCTCGGAGGTGGGTGG | −124~−101 |
| DAPK-P5R | AGCTCCGCGCTCCGGGCTCGCTGGCGCGCTCTACCGCGCACACCCCGC | −169~−216 |
| DAPK-P5F | GGGAGGAGCAGCGAGCGCCGCGCAG | −168~−144 |
| DAPK-P6R | CCCACTCGCCCCACACCCACGCGA | −222~−242 |
| DAPK-P6F | TGTGTGCGGGGTGTGCGCGGTAG | −221~−199 |
| RASSF1A-P1F | TCCTCAGCTCCTTCCCGCCGC | +3~+24 |
| RASSF1A-P1R | GAGCCGCGCAATGGAAACCTG | −20~+2 |
| RASSF1A-P2F | AGCGCGCCCAGCCCCGCCTTC | −60~−40 |
| RASSF1A-P2R | CTCGCAGAGCCCCCCCGCCTTGC | −61~−84 |

TABLE 1-continued

Primers for site-specific methylation of DAPK promoter reporter
construct (SEQ ID NOS. 9-28 top to bottom, respectively):

| PCR primer | Sequence | Position |
|---|---|---|
| RASSF1A-P3F | GGGGTGTGAGGAGGGGA<u>C</u>GA | −119~−100 |
| RASSF1A-P3R | ACCC<u>C</u>GGA<u>C</u>GGCCACAA<u>C</u>GA | −120~−139 |
| RASSF1A-P4F | ATGTGGTGCTTTG<u>C</u>GGT<u>C</u>GC<u>C</u>G | −161~−140 |
| RASSF1A-P4R | C<u>C</u>GGCCCTGGCCCTCCTGGTC<u>C</u>G | −162~−184 |

"Position" refers to transcription start site.
Methylated cytosines are underlined.

Three peptides of historic H1 bound to the DAPK-specific methylated oligo MP1 were identified from mass spectra (not shown). The raw mass spectra were used for protein identification using Proteome Discoverer 1.2, merged and searched against the mammalian NCBI database (May 27, 2011) using the in-house Mascot Protein Search engine. The following parameters for searches were used: trypsin 2 missed cleavages; fixed modification of carbamidomethylation (Cys); variable modifications of deamidation (Asn and Gln) and oxidation (Met); monoisotopic masses; peptide mass tolerance of 3.0 Da; product ion mass tolerance of 0.6 Da. Proteins were considered identified having at least two significant (p<0.05) peptides.

Table 2, Proteins identified from Magnetic bead pull down assay:

In order to identify the responsible proteins binding to the DAPK CpG methylated oligo (MP1), the methylated and unmethylated DNA oligos were immobilized to Dynabeads, and the binding proteins pulled down by affinity purification. Magnetic beads were incubated with biotin-labeled DNA in a binding and washing buffer and incubated with poly(deoxyinosinic-deoxycytidylic) and nuclear extracts of A549 cells in a binding buffer. The bead-DNA-protein complex was precipitated, washed and the bound proteins were released by incubating at high temperature, and chemical reduction. A trypsin digest overnight was followed by direct analysis by LC-MS/MS. LC-MS/MS results were created from the raw mass spectra using Proteome Discoverer 1.2, merged and searched against the mammalian NCBI database using the in-house Mascot Protein Search engine. Proteins were considered identified having at least two significant (p<0.05) peptides The results of LC-MS/MS analysis showed that there are two proteins (histone H1 and heterogeneous nuclear ribonucleoprotein H1) specifically binding to the methylated DNA oligo, and six proteins non-differentially binding to both methylated and unmethylated DNA oligo.

TABLE 2

Proteins identified from Magnetic bead pull down assay

| Identified Protein | DNA binding | | Function |
|---|---|---|---|
| | M-DNA | UM-DNA | |
| vimentin | + | + | Maintaining cell shape, integrity of the cytoplasm, and stabilizing cytoskeletal interactions (22, 23) |
| poly [ADP-ribose] polymerase 1 | + | + | A DNA dependent enzyme involved in the regulation of various important cellular processes such as differentiation, proliferation, and tumor transformation (24-27) |
| ACTG2 | + | + | Involved in various types of cell motility and in the maintenance of the cytoskeleton (28, 29) |
| myosin-9 | + | + | Involved in several important functions, including cytokinesis, cell motility and maintenance of cell shape (30-33) |
| plectin | + | + | Maintaining cell and tissue integrity, orchestrating dynamic changes in cytoarchitecture and cell shape, scaffolding platforms for the assembly, positioning, and regulation of signaling complexes (34-37) |
| histone H1 | + | − | Involved in the formation of higher order chromatin structures, modulate the accessibility of regulatory proteins, chromatin-remodeling factors, and histone modification enzymes to their target sites (25, 38, 39) |
| heterogeneous nuclear ribonucleoprotein H1 | + | − | RNA binding proteins, involved in pre-mRNA processing and mRNA metabolism and transport (40, 41). |

Methods

Primer Design: The CpG(s) in each primer corresponding to the target CpG(s) are methylated. The 5' end of each primer is preferably phosphorylated for purposes of DNA ligation. The primer size can be, for example, up to 60 mers as used in FIG. 4. The forward and reverse primers do not have to be 5' end-adjacent since the DNA extension is circularized.

Figure 5:
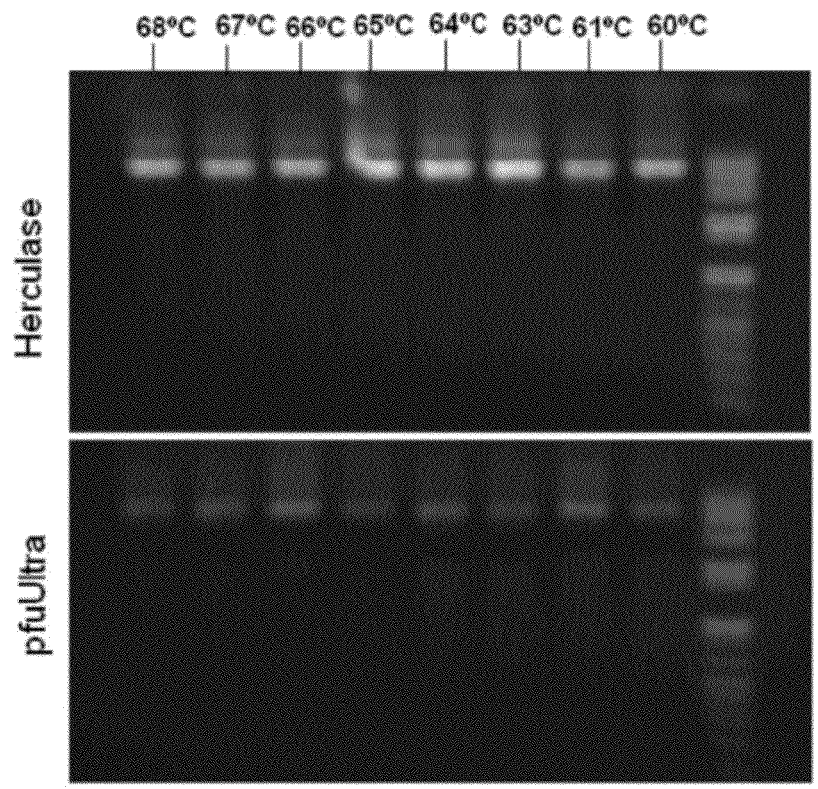
FIG. 5: Optimizing PCR-ligase coupled amplification of DAPK reporter constructs. The yield two reagent approaches for PCR-ligase coupled amplification of DAPK reporter constructs was compared using pfuUltra™ II Fusion HS DNA polymerase (Stratagene) and Herculase® II Fusion DNA polymerase coupled with Taq DNA ligase. The yield of Herculase® II Fusion DNA polymerase coupled with Taq DNA ligase was significantly higher than that of pfuUltra™ II Fusion HS DNA polymerase.
Figure 6:
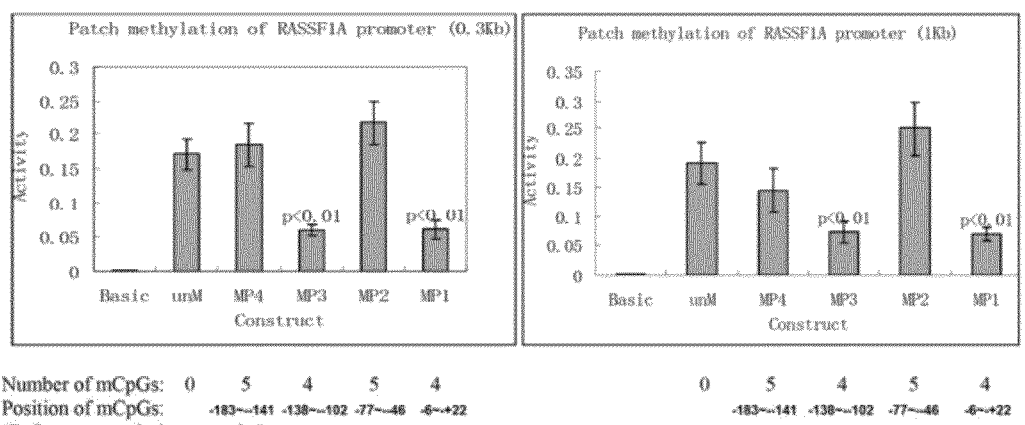
FIG. 6: Functional analysis of DNA methylation impact on RASSF1A promoter reporter constructs. Unmethylated RASSF1A reporter constructs (unM) and four site-specific methylated reporter constructs (MP1 to MP4) were transfected into A549 cells. PRL-TK which expresses Renilla luciferase was co-transfected as an internal control. The empty vector (Basic) was also transfected as negative control. All constructs were transfected in triplicates. After 36 hours, luciferase activities were determined by dual luciferase assay. Firefly luciferase activity was normalized to Renilla luciferase activity (internal control). Here, each of two clusters, each containing four methylated CpGs at +21, +15, +2, −6 and −138, −129, −125, −102, with reference to TSS, appear to halve promoter activity. P values represent t test comparisons with the unmethylated RASSF1A promoter insert (unM) control. Basic: the reporter construct without promoter; unM: The reporter construct with unmethylated RASSF1A promoter; MP1 to MP4: reporter constructs with RASSF1A promoter methylated at different CpG sites; mCpG: Methylated CpG.
Figure 7:
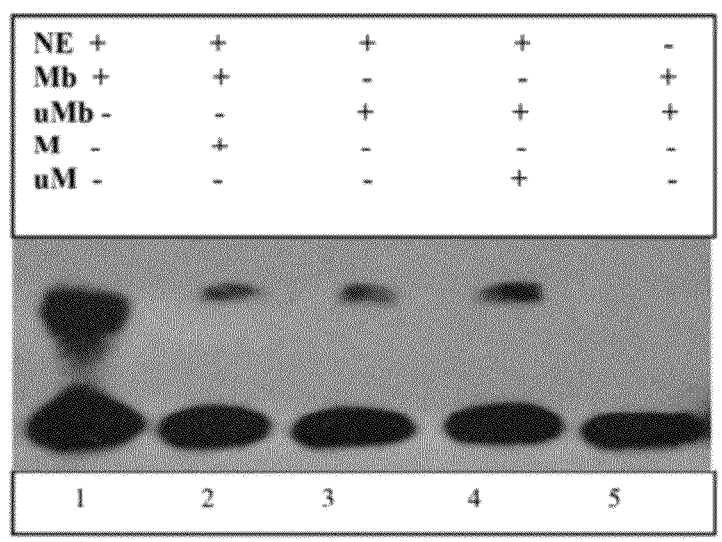
FIG. 7. LightShift EMSA for biotin-labeled methylated and unmethylated MP1 oligo DNA from the DAPK promoter. Lane 1: Nuclear extract proteins specifically bind to the methylated MP1 DNA. Lane 2: The binding of nuclear extract proteins to the methylated DNA was competed with unlabeled methylated MP1 DNA. Lane 3: Nuclear extract proteins nonspecifically bind to unmethylated MP1 oligo DNA. Lane 4: The nonspecific binding of nuclear extract proteins to the unmethylated DNA was not competed with unlabeled unmethylated MP1 DNA. Lane 5: MP1 oligo DNA only as negative control. NE: nuclear extracts; Mb: methylated DNA labeled with biotin; M: methylated DNA unlabeled; uMb: unmethylated DNA labeled with biotin; uM: unmethylated DNA unlabeled.

DNA polymerase and Taq DNA ligase: Taq DNA ligase is available from New England Biolabs (Ipswich, Mass.). Different DNA polymerases can be coupled in the reaction sequence with this DNA ligase. Four high-fidelity DNA polymerases were tested herein: AccuPrime™ HF DNA polymerase (Invitrogen (now Life Technologies), Carlsbad, Calif.); Phusion® high fidelity DNA polymerase (New England Biolabs, Ipswich, Mass.); pfuUltra™ II Fusion HS DNA polymerase (Stratagene (now Agilent), Santa Clara, Calif.); and Herculase® II Fusion DNA polymerase. Based on the yield of the ligated PCR product, Herculase® II Fusion DNA polymerase gave the best results and was used in the experiments described herein. The ligated PCR product was 200 ng to 500 ng per 50 µl PCR reaction (FIG. 5).

Human DNA (cytosine-5) methyltransferase (Dnmt1): Dnmt1 can be used for specifically methylating the complementary strand of the methylated primers. Human DNA (cytosine-5) methyltransferase as used is herein is available from New England Biolabs, Ipswich, Mass. Dnmt1 is also available from Active Motif, Carlsbad, Calif.

REFERENCES

Castanotto et al., *Mol. Ther.* 12; 179-183, (2005).
Curradi et al. "Molecular Mechanisms of Gene Silencing Mediated by DNA Methylation," *Mol. Cell Biol.* 22, 3157-3173, (2002).
Kawasaki et al., *Nature* 431; 211, (2004).
Kawasaki et al., *Nature* 441; 1176, (2006).
Li et al., *Nucleic Acids Res.* 35:100-112, (2007).
Meister et al., *Nucleic Acids Res.* 38:1749-59 (2010).
Morris et al., *Science.* 305:1289-92, (2004).
Suzuki et al., J. RNAi *Gene Silencing* 1; 66-78, (2005).
Smith et al., *J. Biol. Chem.* 283: 9878-9885, (2008).
Smith et al., *Nucleic Acids Res.* 35:740-754, (2007).

What is claimed is:

1. A method for determining the effect of C-5 methylating one or more predetermined cytosine nucleotide residues of a deoxyribonucleic acid (DNA) on expression of a gene of interest comprising the steps of:
   a) denaturing a circular double-stranded DNA construct, wherein a cytosine residue of one of the strands of the circular DNA construct corresponds to the predetermined cytosine nucleotide residue and wherein the circular DNA construct comprises a nucleotide sequence identical to the gene of interest;
   b) hybridizing each of a pair of primers to separate strands of the denatured circular DNA construct, wherein each primer comprises a 5' phosphate, and wherein at least one of the primers is C-5 methylated at a cytosine nucleotide residue thereof which is (i) immediately 5' to a guanine nucleotide residue of the primer, and (ii) complementary to a guanine nucleotide residue of the strand of the circular DNA construct immediately 3' to the cytosine nucleotide residue of the DNA construct which corresponds to the predetermined cytosine nucleotide residue;
   c) contacting the hybridized primers resulting from step b) with a DNA polymerase, deoxynucleoside triphosphates, and a plurality of copies of the pair of primers under conditions permitting a polymerase chain reaction to occur, thereby producing a plurality of nicked copies of the circular DNA construct, wherein each strand of each nicked copy incorporates a primer comprising a 5' phosphate and wherein at least one strand of each nicked copy incorporates the C-5 methylated primer;
   d) contacting at least one copy of the plurality of nicked copies with a DNA ligase so as to form a phosphodiester bond between the 5' phosphate of each incorporated primer of each strand and each respective 3' end of each strand of the at least one copy so as to thereby form a copy of the circular DNA construct;
   e) contacting the copy of the circular DNA construct with a methyltransferase enzyme so as to thereby C-5 methylate the cytosine nucleotide residue immediately 5' to the guanine nucleotide residue which is hybridized to the C-5 methylated cytosine nucleotide residue of the C-5 methylated primer incorporated into the copy of the circular DNA construct;

f) transfecting a cell with the C-5 methylated circular DNA construct resulting from step e); and g) quantifying expression by the cell of the gene of interest, thereby determining the effect of C-5 methylating the one or more predetermined cytosine nucleotide residues of the deoxyribonucleic acid on expression of the gene of interest.

2. The method of claim 1, wherein the quantified expression of the gene of interest in step g) is compared to a quantified expression of the gene of interest of a non-C-5 methylated control.

3. A method for making a deoxyribonucleic acid (DNA) which is C-5 methylated at a predetermined cytosine nucleotide residue thereof comprising the steps of:

a) denaturing a circular double-stranded DNA construct, wherein a cytosine residue of one of the strands of the circular DNA construct corresponds to the predetermined cytosine nucleotide residue;

b) hybridizing each of a pair of primers to separate strands of the denatured circular DNA construct, wherein each primer comprises a 5' phosphate, and wherein at least one of the primers is C-5 methylated at a cytosine nucleotide residue thereof which is (i) immediately 5' to a guanine nucleotide residue of the primer, and (ii) complementary to a guanine nucleotide residue of the strand of the circular DNA construct immediately 3' to the cytosine nucleotide residue of the DNA construct which corresponds to the predetermined cytosine nucleotide residue;

c) contacting the hybridized primers resulting from step b) with a DNA polymerase, deoxynucleoside triphosphates, and a plurality of copies of the pair of primers under conditions permitting a polymerase chain reaction to occur, thereby producing a plurality of nicked copies of the circular DNA construct, wherein each strand of each nicked copy incorporates a primer comprising a 5' phosphate and wherein at least one strand of each nicked copy incorporates the C-5 methylated primer;

d) contacting at least one copy of the plurality of nicked copies with a DNA ligase so as to form a phosphodiester bond between the 5' phosphate of each incorporated primer of each strand and each respective 3' end of each strand of the at least one copy so as to thereby form a copy of the circular DNA construct; and e) contacting the copy of the circular DNA construct with a methyltransferase enzyme so as to thereby C-5 methylate the cytosine nucleotide residue immediately 5' to the guanine nucleotide residue which is hybridized to the C-5 methylated cytosine nucleotide residue of the C-5 methylated primer incorporated into the copy of the circular DNA construct, so as to thereby make the deoxyribonucleic acid which is C-5 methylated at the predetermined cytosine nucleotide residue.

4. The method of claim 1, further comprising, subsequent to step e), digesting deoxyribonucleic acids in a reaction mixture resulting from steps a) through d) or steps a) through e) which deoxyribonucleic acids comprise a 5'-$G^{me6}$ATC-3' sequence by contacting the deoxyribonucleic acids which comprise a 5'-$G^{me6}$ATC-3' sequence with a Dpn1 enzyme under conditions permitting digestion of deoxyribonucleic acids.

5. The method of claim 1, wherein the DNA ligase is Taq DNA ligase.

6. The method of claim 1, wherein the deoxynucleoside triphosphates are selected from dATP, dCTP, dGTP and dTTP.

7. The method of claim 1, further comprising (i) before step e) digesting linear deoxyribonucleic acids in a reaction mixture resulting from steps a) through d), or (ii) after step e) digesting linear deoxyribonucleic acids in a reaction mixture resulting from steps a) through e), by contacting the linear deoxyribonucleic acids in the reaction mixture with an exonuclease.

8. The method of claim 7, wherein the exonuclease is T7 exonuclease.

9. The method of claim 1, wherein the methyltransferase enzyme is specific for hemi-methylated double-stranded DNA.

10. The method of claim 1, wherein the methyltransferase enzyme is human DNA (cytosine-5) methyltransferase (Dnmt1).

11. The method of claim 1, wherein the circular DNA construct comprises a promoter sequence.

12. The method of claim 1, wherein the deoxyribonucleic acid which is C-5 methylated at the predetermined cytosine nucleotide residue is, or comprises, a promoter sequence.

13. The method of claim 1, wherein a portion of the DNA construct comprises a nucleic acid sequence derived from *Escherichia coli*.

14. The method of claim 1, wherein at least one of the primers is from 18 to 30 nucleotide residues in length.

15. The method of claim 1, wherein at least one of the primers is from 31 to 65 nucleotide residues in length.

16. The method of claim 1, wherein the DNA construct comprises a nucleic acid sequence encoding a reporter protein.

17. The method of claim 16, wherein the reporter protein is a luciferase, a chloramphenicol transferase, a green fluorescent protein, a beta-galactosidase, or a recombinant human growth hormone, or other reporter/detectable gene.

18. The method of claim 1, wherein at least one primer is C-5 methylated at the cytosine nucleotide residue of every cytosine-guanine dinucleotide thereof.

19. The method of claim 1, further comprising bisulfite sequencing the deoxyribonucleic acid which is C-5 methylated at the predetermined cytosine nucleotide residue so as to confirm the C-5 methylation.

20. A method for determining the effect of C-5 methylating one or more predetermined cytosine nucleotide residues of cytosine-guanine dinucleotides of a deoxyribonucleic acid on expression of the deoxyribonucleic acid comprising C-5 methylating the one or more predetermined cytosine nucleotide residues by the method of claim 3, and then quantifying the expression of the deoxyribonucleic acid, so as to thereby determine the effect of C-5 methylating the one or more predetermined cytosine nucleotide residues of cytosine-guanine dinucleotides of the deoxyribonucleic acid on expression of the deoxyribonucleic acid.

* * * * *

SEQUENCE LISTING

```
<160> NUMBER OF SEQ ID NOS: 28

<210> SEQ ID NO 1
<211> LENGTH: 70
<212> TYPE: DNA
<213> ORGANISM: Artificial
<220> FEATURE:
<223> OTHER INFORMATION: reporter construct based on firefly gene

<400> SEQUENCE: 1
ccgccagccc gcttgcaggg tccccattgg ccgcctgccg gccgccctcc gcccaaaagg      60
cggcaaggag                                                            70

<210> SEQ ID NO 2
<211> LENGTH: 71
<212> TYPE: DNA
<213> ORGANISM: Artificial
<220> FEATURE:
<223> OTHER INFORMATION: reporter construct based on firefly gene

<400> SEQUENCE: 2
tgaggaatgg tggaaaattt gcttttgct ggctgtttgc tggttatttt tgggatgttt      60
gtttgattgt t                                                          71

<210> SEQ ID NO 3
<211> LENGTH: 70
<212> TYPE: DNA
<213> ORGANISM: Artificial
<220> FEATURE:
<223> OTHER INFORMATION: reporter construct based on firefly gene

<400> SEQUENCE: 3
ccgccagccc gcttgcaggg tccccattgg ccgcctgccg gccgccctcc gcccaaaagg      60
cggcaaggag                                                            70

<210> SEQ ID NO 4
<211> LENGTH: 70
<212> TYPE: DNA
<213> ORGANISM: Artificial
<220> FEATURE:
<223> OTHER INFORMATION: reporter construct based on firefly gene

<400> SEQUENCE: 4
gaggaatggt ggaaaatttg cttttgctg gctgtttgct ggttattttt gggatgtttg      60
tttgattgtt                                                            70

<210> SEQ ID NO 5
<211> LENGTH: 70
<212> TYPE: DNA
<213> ORGANISM: Artificial
```

```
<220> FEATURE:
<223> OTHER INFORMATION: Reporter construct based on firefly gene

<400> SEQUENCE: 5
ctccttgccg ccttttgggc ggagggcggc cggcaggcgg ccaatgggga ccctgcaagc      60
gggctggcgg                                                            70

<210> SEQ ID NO 6
<211> LENGTH: 70
<212> TYPE: DNA
<213> ORGANISM: Artificial
<220> FEATURE:
<223> OTHER INFORMATION: reporter construct based on firefly gene

<400> SEQUENCE: 6
ggtggttggg tgaatgtttt aggggtaatt ggcggatggc tggcgggagg cgggttttttt    60 gttgtttttt                                                            70

<210> SEQ ID NO 7
<211> LENGTH: 22
<212> TYPE: DNA
<213> ORGANISM: Artificial
<220> FEATURE:
<223> OTHER INFORMATION: Pimer directed to human DAPK

<400> SEQUENCE: 7
gccgcctgcc ggccgccctc cg                                              22

<210> SEQ ID NO 8
<211> LENGTH: 21
<212> TYPE: DNA
<213> ORGANISM: Artificial
<220> FEATURE:
<223> OTHER INFORMATION: Pimer directed to human DAPK

<400> SEQUENCE: 8
caatggggac cctgcaagcg g                                               21

<210> SEQ ID NO 9
<211> LENGTH: 32
<212> TYPE: DNA
<213> ORGANISM: Artificial
<220> FEATURE:
<223> OTHER INFORMATION: primer directed to human DAPK

<400> SEQUENCE: 9
cactccgaag cagcctctcg gctccttgcc gc                                   32

<210> SEQ ID NO 10
<211> LENGTH: 23
<212> TYPE: DNA
<213> ORGANISM: Artificial
<220> FEATURE:
<223> OTHER INFORMATION: Primer directed to human DAPK

<400> SEQUENCE: 10
tgaggaggac agccggaccg agc                                             23

<210> SEQ ID NO 11
<211> LENGTH: 25
<212> TYPE: DNA
<213> ORGANISM: Artificial
<220> FEATURE:
<223> OTHER INFORMATION: Primer directed to human DAPK
```

```
<400> SEQUENCE: 11
tgggcggagg gcggccggca ggcgg                                              25

<210> SEQ ID NO 12
<211> LENGTH: 24
<212> TYPE: DNA
<213> ORGANISM: Artificial
<220> FEATURE:
<223> OTHER INFORMATION: primer directed to human DAPK

<400> SEQUENCE: 12
aaaggcggca aggagccgag aggc                                               24

<210> SEQ ID NO 13
<211> LENGTH: 36
<212> TYPE: DNA
<213> ORGANISM: Artificial
<220> FEATURE:
<223> OTHER INFORMATION: Pimer directed to human DAPK

<400> SEQUENCE: 13
gcaagcgggc tggcggcgcg gcccacccac ctccga                                  36

<210> SEQ ID NO 14
<211> LENGTH: 24
<212> TYPE: DNA
<213> ORGANISM: Artificial
<220> FEATURE:
<223> OTHER INFORMATION: primer directed to human DAPK

<400> SEQUENCE: 14
agggtcccca ttggccgcct gccg                                               24

<210> SEQ ID NO 15
<211> LENGTH: 34
<212> TYPE: DNA
<213> ORGANISM: Artificial
<220> FEATURE:
<223> OTHER INFORMATION: primer directed to human DAPK

<400> SEQUENCE: 15
caggccggcg ctgcgggttc tgcgcggcgc tcgc                                    34

<210> SEQ ID NO 16
<211> LENGTH: 24
<212> TYPE: DNA
<213> ORGANISM: Artificial
<220> FEATURE:
<223> OTHER INFORMATION: primer directed to human DAPK

<400> SEQUENCE: 16
gcagggcagc tcggaggtgg gtgg                                               24

<210> SEQ ID NO 17
<211> LENGTH: 48
<212> TYPE: DNA
<213> ORGANISM: Artificial
<220> FEATURE:
<223> OTHER INFORMATION: Primer directed to human DAPK

<400> SEQUENCE: 17
agctccgcgc tccgggctcg ctggcgcgct ctaccgcgca caccccgc                     48
```

```
<210> SEQ ID NO 18
<211> LENGTH: 25
<212> TYPE: DNA
<213> ORGANISM: Artificial
<220> FEATURE:
<223> OTHER INFORMATION: primer directed to human DAPK

<400> SEQUENCE: 18
gggaggagca gcgagcgccg cgcag                                              25

<210> SEQ ID NO 19
<211> LENGTH: 24
<212> TYPE: DNA
<213> ORGANISM: Artificial
<220> FEATURE:
<223> OTHER INFORMATION: primer directed to human DAPK

<400> SEQUENCE: 19
cccactcgcc ccacacccac gcga                                               24

<210> SEQ ID NO 20
<211> LENGTH: 23
<212> TYPE: DNA
<213> ORGANISM: Artificial
<220> FEATURE:
<223> OTHER INFORMATION: primer directed to human DAPK

<400> SEQUENCE: 20
tgtgtgcggg gtgtgcgcgg tag                                                23

<210> SEQ ID NO 21
<211> LENGTH: 21
<212> TYPE: DNA
<213> ORGANISM: Artificial
<220> FEATURE:
<223> OTHER INFORMATION: primer directed to human RASSF1A

<400> SEQUENCE: 21
tcctcagctc cttcccgccg c                                                  21

<210> SEQ ID NO 22
<211> LENGTH: 21
<212> TYPE: DNA
<213> ORGANISM: Artificial
<220> FEATURE:
<223> OTHER INFORMATION: Primer directed to human RASSF1A

<400> SEQUENCE: 22
gagccgcgca atggaaacct g                                                  21

<210> SEQ ID NO 23
<211> LENGTH: 21
<212> TYPE: DNA
<213> ORGANISM: Artificial
<220> FEATURE:
<223> OTHER INFORMATION: Primer directed to human RASSF1A

<400> SEQUENCE: 23
agcgcgccca gccccgcctt c                                                  21

<210> SEQ ID NO 24
<211> LENGTH: 24
<212> TYPE: DNA
<213> ORGANISM: Artificial
<220> FEATURE:
<223> OTHER INFORMATION: Primer directed to human RASSF1A
```

```
<400> SEQUENCE: 24
ctcgcagagc cccccccgcc ttgc                                          24

<210> SEQ ID NO 25
<211> LENGTH: 20
<212> TYPE: DNA
<213> ORGANISM: Artificial
<220> FEATURE:
<223> OTHER INFORMATION: Primer directed to human RASSF1A

<400> SEQUENCE: 25
ggggtgtgag gaggggacga                                               20

<210> SEQ ID NO 26
<211> LENGTH: 20
<212> TYPE: DNA
<213> ORGANISM: Artificial
<220> FEATURE:
<223> OTHER INFORMATION: Primer directed to human RASSF1A

<400> SEQUENCE: 26
accccggacg gccacaacga                                               20

<210> SEQ ID NO 27
<211> LENGTH: 22
<212> TYPE: DNA
<213> ORGANISM: Artificial
<220> FEATURE:
<223> OTHER INFORMATION: Primer directed to human RASSF1A

<400> SEQUENCE: 27
atgtggtgct ttgcggtcgc cg                                            22

<210> SEQ ID NO 28
<211> LENGTH: 23
<212> TYPE: DNA
<213> ORGANISM: Artificial
<220> FEATURE:
<223> OTHER INFORMATION: Primer directed to human RASSF1A

<400> SEQUENCE: 28
ccggccctgg ccctcctggt ccg                                           23
```